(12) United States Patent
Chavakula

(10) Patent No.: US 10,856,782 B2
(45) Date of Patent: Dec. 8, 2020

(54) MULTI-USE MONITOR

(71) Applicant: Anand Kumar Chavakula, Hyattsville, MD (US)

(72) Inventor: Anand Kumar Chavakula, Hyattsville, MD (US)

(*) Notice: Subject to any disclaimer, the term of this patent is extended or adjusted under 35 U.S.C. 154(b) by 126 days.

(21) Appl. No.: 16/287,066

(22) Filed: Feb. 27, 2019

(65) Prior Publication Data

US 2020/0196916 A1    Jun. 25, 2020

Related U.S. Application Data

(60) Provisional application No. 62/917,619, filed on Dec. 19, 2018.

(51) Int. Cl.

| | | |
|---|---|---|
| *A61B 5/15* | (2006.01) | |
| *A61B 5/145* | (2006.01) | |
| *A61B 5/00* | (2006.01) | |
| *A61B 5/157* | (2006.01) | |
| *A61B 5/151* | (2006.01) | |
| *A61B 5/0205* | (2006.01) | |
| *G01N 33/49* | (2006.01) | |
| *G16H 40/63* | (2018.01) | |

(52) U.S. Cl.
CPC .......... *A61B 5/1411* (2013.01); *A61B 5/0006* (2013.01); *A61B 5/0015* (2013.01); *A61B 5/14532* (2013.01); *A61B 5/157* (2013.01); *A61B 5/15107* (2013.01); *A61B 5/150748* (2013.01); *A61B 5/6831* (2013.01); *A61B 5/02055* (2013.01); *A61B 5/742* (2013.01); *A61B 2562/0295* (2013.01); *G01N 33/49* (2013.01); *G16H 40/63* (2018.01)

(58) Field of Classification Search
CPC ... A61B 5/1411; A61B 5/1405; A61B 5/1416; A61B 5/1427; A61B 5/15; A61B 5/150236; A61B 5/150763; A61B 5/15165; A61B 5/15173; A61B 5/150183; A61B 5/150358; A61B 5/150847; G01N 33/49
See application file for complete search history.

(56) References Cited

U.S. PATENT DOCUMENTS

| | | | |
|---|---|---|---|
| 6,196,979 B1 * | 3/2001 | Virtanen .......... | G01N 33/54373 600/573 |
| 6,620,112 B2 * | 9/2003 | Klitmose ............. | G01N 33/528 422/410 |

(Continued)

*Primary Examiner* — Matthew F Desanto

(57) ABSTRACT

A health monitoring system comprises a housing, a test strip assembly, a lancet, a transparent cover, and a monitor. The test strip assembly is configured to detect concentration of the sample of the blood, using lancet. It also has multiple ways to test blood like a laser-based system and a wireless based blood measuring system. Further, it has a heart rate monitor system, blood pressure and weight measuring rechargeable straps, wireless systems for information exchange with other devices, two way communication systems, a flash light, a removable X-Ray lens system, an auto created individual profile system based on a multi-factor authentication system that is capable of automatic grouping of all test results or any data created by a user, auto retrieving from a remote computer server and auto installing on a device based on its limitations through onboard multi-factor authentications systems.

13 Claims, 23 Drawing Sheets

(56) References Cited

U.S. PATENT DOCUMENTS

| | | | | |
|---|---|---|---|---|
| 6,989,891 B2* | 1/2006 | Braig | A61B 5/150717 | |
| | | | 356/39 | |
| 7,214,200 B2* | 5/2007 | Raney | A61B 5/150022 | |
| | | | 600/573 | |
| 7,247,144 B2* | 7/2007 | Douglas | A61B 5/14532 | |
| | | | 600/583 | |
| 7,909,775 B2* | 3/2011 | Alden | A61B 5/150832 | |
| | | | 600/573 | |
| 8,007,445 B2* | 8/2011 | Harttig | A61B 5/150664 | |
| | | | 600/583 | |
| 8,092,385 B2* | 1/2012 | Goldberger | A61B 5/15003 | |
| | | | 600/365 | |
| 8,435,190 B2* | 5/2013 | Freeman | A61B 5/157 | |
| | | | 600/583 | |
| 8,562,558 B2* | 10/2013 | Kamath | A61B 5/14546 | |
| | | | 604/66 | |
| 8,602,991 B2* | 12/2013 | Stafford | A61B 5/14532 | |
| | | | 600/309 | |
| 8,613,703 B2* | 12/2013 | Stafford | A61B 5/1473 | |
| | | | 600/309 | |
| 8,852,101 B2* | 10/2014 | Stafford | A61B 5/0015 | |
| | | | 600/309 | |
| 9,237,867 B2* | 1/2016 | Richter | A61B 5/150305 | |
| 9,521,968 B2* | 12/2016 | Mazza | A61B 5/14532 | |
| 9,717,452 B2* | 8/2017 | Roe | A61B 5/15113 | |
| 9,782,114 B2* | 10/2017 | Reynolds | A61B 5/150114 | |
| 10,736,547 B2* | 8/2020 | Stafford | A61B 5/1451 | |
| 2003/0211619 A1* | 11/2003 | Olson | A61B 5/150358 | |
| | | | 436/44 | |
| 2004/0191119 A1* | 9/2004 | Zanzucchi | A61B 5/14514 | |
| | | | 422/504 | |
| 2006/0079810 A1* | 4/2006 | Patel | A61B 5/14532 | |
| | | | 600/583 | |
| 2013/0053660 A1* | 2/2013 | Shieh | A61B 5/15171 | |
| | | | 600/309 | |
| 2017/0020424 A1* | 1/2017 | Holweg | A61B 5/14539 | |
| 2019/0015031 A1* | 1/2019 | Liepold | B01L 3/5082 | |

* cited by examiner

MULTI-USE MONITOR

CROSS-REFERENCE TO RELATED APPLICATION

The present utility patent application claims the priority benefit OF U.S. provisional patent application Ser. No. 62/917,619 filed on Dec. 19, 2018, the entirety of which is incorporated herein by reference for all purposes.

BACKGROUND OF THE INVENTION

A. Technical Field

The present invention generally relates to a health monitoring system. Specifically, the present invention relates to a health monitoring system that includes a combination of a test strip assembly with a lancet, configured to monitor the concertation of a blood sample of a user.

B. Description of Related Art

Medical devices are used for medical diagnostics and therapeutic treatments for improving the health condition of patients. Many medical devices could be manufactured and operated with software technologies. Such devices could be used to evaluate medical samples for diagnostic purposes and to test various non-medical samples. In many fields of healthcare, repeated monitoring of certain medical conditions of the patient, such as blood glucose concentration is of particular importance. For example, a medical diagnostic meter/equipment is used for monitoring blood glucose concentration. The measurement of blood glucose concentration is important for diagnosing, treating or controlling a variety of disorders of the patients. One special case of concern for example is a patient affected by diabetes who may need to measure very frequently the concentration of glucose in order to respond promptly with the correct medication.

In clinal centers and institutes that use blood test devices for testing and monitoring blood glucose levels, the blood samples of the patients are tested using a test strip that contains appropriate reagents for creating the chemical reactions necessary to measure glucose levels, which is subsequently analyzed by a blood glucose monitor. However, it is difficult for patients to check their blood several times a day at a clinic or medical institution.

Further, the patient could find it difficult to use the existing blood test device at home and then manually records the parameters, time and date in a log book continuously for taking appropriate medicines. The patient could also find it inconvenient and cumbersome to use all the various equipment that may include a plurality of lancers, test strips and a blood glucose monitor. Further, the existing test devices lack in convenient and flexible adjustability for the patient.

Accordingly, there is a need for a health monitoring system that includes a combination of a plurality of a finger pricking device with a test strip assembly that can make it is easy to use for monitoring the blood glucose level. There is also a need for a health monitoring system to measure blood pressure, heart rate, height, and weight of the patient or user. There is also a need for a health monitoring system for automatically storing and recording the readings of the blood glucose levels and other health test data of a patient every single time in one user profile. There is also a need for a health monitoring system to create a unique profile for the patient based on the blood type and an authentication system. Further, there is also a need for a health monitoring system to provide convenient and flexible adjustability for the patient while using the same system.

SUMMARY OF THE INVENTION

The present invention generally discloses a health monitoring system. The present invention that is directed to a health monitoring system includes a combination of test strip assembly with a lancet, configured to monitor the concertation of a blood sample of a user.

In one embodiment, the system comprises a housing, a test strip assembly, a finger pricking device, a transparent cover, and a monitor. In one embodiment, the housing includes a top portion and a bottom portion. In one embodiment, the test strip assembly is disposed in the bottom portion of the housing. In one embodiment, the test strip assembly comprises a tapered side on, but not limited to, any one of the sides. The test strip assembly is configured to detect a concentration of the sample of the blood of the user.

In one embodiment, the finger pricking device is disposed on an extended edge of the tapered side of the test strip assembly. In one embodiment, the finger pricking device is integrated to a plunger to prick a body part of a user via a plunger mechanism for availing a blood sample. In one embodiment, the finger pricking device is disposed in a center portion of the test strip assembly. In another embodiment, the finger pricking device is disposed on any one of the side portions of the test strip assembly.

In one embodiment, the transparent cover is disposed at a bottom portion of the test strip assembly. In one embodiment, the transparent cover is in a half-opened shaped structure to access the test strip assembly and insert the finger pricking device. The transparent cover comprises an angular shape at a bottom portion and also opened on the side to insert the test strip assembly without opening the transparent cover.

In one embodiment, the monitor is disposed in the housing. In one embodiment, the monitor is configured to display the concentration of the blood sample. In one embodiment, the monitor further comprises a processor and a memory unit. In one embodiment, the monitor is at least one of a computer, a smartphone, a PDA, a tablet, a credit card terminal, a point of sale terminal (POS), an entertainment device or TV, a medical terminal, and a travel terminal. In one embodiment, the system further comprises a server and a database that is in communication with the monitor for storing information related to the concentration of the blood sample and related test parameters of a user. The memory unit stores a set of program modules, and the processor is in communication with the memory unit, configured to execute the appropriate set of program modules.

In one embodiment, the appropriate set of program modules comprises a profile creation module, a description generation module, and an output module. In one embodiment, the profile creation module is configured to automatically create a profile of the user via a multi-factor authentication system. The multi-factor authentication system is configured to authenticate the user for logging into the user's profile. In one embodiment, the description generation module is configured to convert the information related to the concentration of the blood sample and related test parameters into a readable description. In one embodiment, the output module is configured to present a readable description to the user.

In one embodiment, the multi-factor authentication system to authenticate the user for logging into the system, wherein the multi-factor authentication system includes a fingerprint authentication, a contactless fingerprint authentication, a facial feature authentication, and a password-based authentication.

In one embodiment, the monitor is wirelessly communicated to a user communication device via a network, wherein the network includes at least one of Wi-Fi, Bluetooth®, WLAN, infrared, and radio waves. In one embodiment, the user communication device is at least one of a tablet, a smartphone, PDA, a smartwatch, a computer, and a laptop. In one embodiment, the monitor further comprises a plurality of input and output ports, wherein the plurality of input and output ports are configured to transmit and receive the information related to the concentration of the blood sample and related test parameters of the user to other user communication devices.

In one embodiment, the system further comprises blood pressure straps and a removable camera lens. The blood pressure straps are also configured to measure the weight of the user. The straps can be removed from the device and placed under any person or object to be measured based on the pressure and weight of the person or object and upon the detection of the object's weight, the strap can wirelessly send the information to the invention for further readout. Further, the blood pressure straps can be rechargeable via a wireless power transmission system or when directly attached to the main embodiment or device. In one embodiment, the removable camera lens is configured to create X-ray images for diagnosing the user's body.

In one embodiment, the system further comprises a height measuring detector light and a heart rate monitor. The height measuring detector light is configured to measure the height of the user. The heart rate monitor is configured to monitor and track the heart rate of the user.

In one embodiment, the housing further includes a plurality of slots, wherein the plurality of slots is configured to store the test strip assembly, finger pricking devices, and alcohol strips for cleaning the part of the user's body. In one embodiment, the system further comprises an emergency alerting system, wherein the emergency alerting system includes an audio and video call button with GPS auto-location.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The embodiments herein will be better understood from the following detailed description with reference to the drawings, in which.

DETAILED DESCRIPTION OF EMBODIMENTS

A description of embodiments of the present invention will now be given with reference to the Figures. It is expected that the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Figure 1:
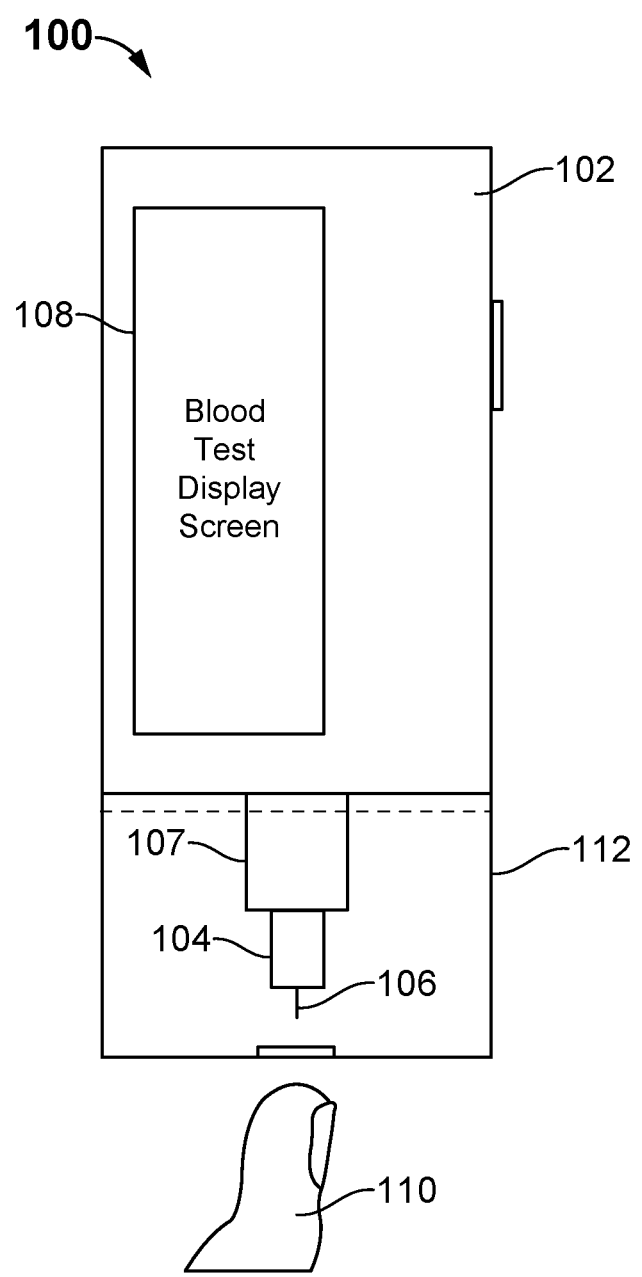
FIG. 1 shows a side view of a health monitor system in an embodiment of the present invention.

Referring to FIG. 1, a health monitoring system 100 is configured to monitor the health of a user. In one embodiment, the system 100 is a portable information handling system. In one embodiment, the system 100 comprises a housing 102, a test strip assembly 104, a finger pricking device 106, and a monitor 108. In one embodiment, housing 102 comprises a top portion and a bottom portion. In one embodiment, the test strip assembly 104 is disposed in the bottom portion of the housing 102. The test strip assembly 104 is configured to detect a concentration of a blood sample. In one embodiment, the finger pricking device 106 is disposed in the test strip assembly 104. The finger pricking device 106 is configured to prick a body part, for example, a finger 110 of a user or patient. In one embodiment, the finger pricking device 106 is further integrated to a plunger 107 to prick a body part, for example, a finger 110 of the user via a plunger mechanism for availing a blood sample.

In one embodiment, the monitor 108 is disposed in the housing 102 of the system 100. The monitor 108 is configured to display the concentration of the sample of the blood. In one embodiment, the monitor 108 further comprises a processor and a memory unit. In one embodiment, the monitor 108 is at least one of a computer, a smartphone, a PDA, a tablet, a credit card terminal, a point of sale terminal (POS), an entertainment device or TV, a medical terminal, and a travel terminal. In one embodiment, the system 100 further comprises a server and database that is in communication with the monitor 108 for storing information related to the concentration of the blood sample and related test parameters of a user. The memory unit stores a set of program modules, and the processor is in communication with the memory unit, configured to execute the set of program modules.

In one embodiment, the set of program modules comprises a profile creation module, a description generation module, and an output module. In one embodiment, the profile creation module is configured to automatically create a profile of the user via a multi-factor authentication system. The multi-factor authentication system is configured to automatically authenticate the user for logging into the user's profile. In one embodiment, the description generation module is configured to convert the information related to the concentration of the blood sample and related test parameters into a readable description. In one embodiment, the output module is configured to present a readable description to the user.

The finger pricking device 106 is positioned in a case cover 114. In one embodiment, the finger pricking device 106 is stored in the case cover 114 and the tip of the finger pricking device 106 could be covered by a cap 116. In one embodiment, the finger pricking device 106 is a lancet or a needle.

Figure 2:
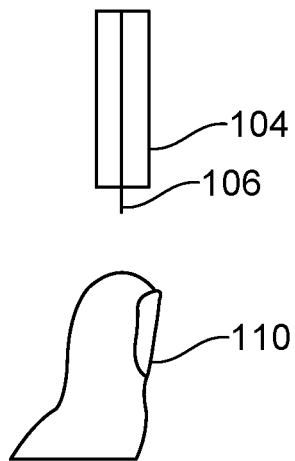
FIG. 2 shows a side view of a combination of the finger pricking device with a test strip assembly in one embodiment of the present invention.

Referring to FIG. 2, a combination of the test strip assembly 104 and the finger pricking device 106. The finger pricking device 106 is used to prick a finger 110 for availing a blood sample. In one embodiment, the finger pricking device 106 could be removed from the test strip assembly 104 for inserting a new lancet. The blood sample of the user is placed on the test strip assembly 104 for testing and detecting the blood glucose level.

Figure 3:
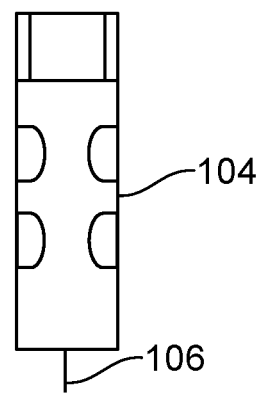
FIG. 3 shows a side view of the finger pricking device disposed in a center portion of a test strip assembly in one embodiment of the present invention.
Figure 4:
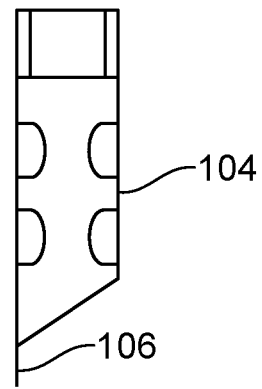
FIG. 4 shows a side view of the finger pricking device disposed on an extended edge of the tapered side of the test strip assembly in another embodiment of the present invention.

Referring to FIG. 3, the finger pricking device 106 is disposed in a center portion of the test strip assembly 104. The user could place a blood drop on the test strip assembly for detecting the concentration of the sample of the blood. Referring to FIG. 4, the test strip assembly 104 comprises a tapered side. In another embodiment, the finger pricking device 106 is disposed on an extended edge of the tapered side of the test strip assembly 104. In one embodiment, the test strip assembly 104 comprises a tapered side on, but not limited to, any one side portion. In another embodiment, the test strip assembly 104 comprises a tapered side at a bottom portion.

Figure 5:
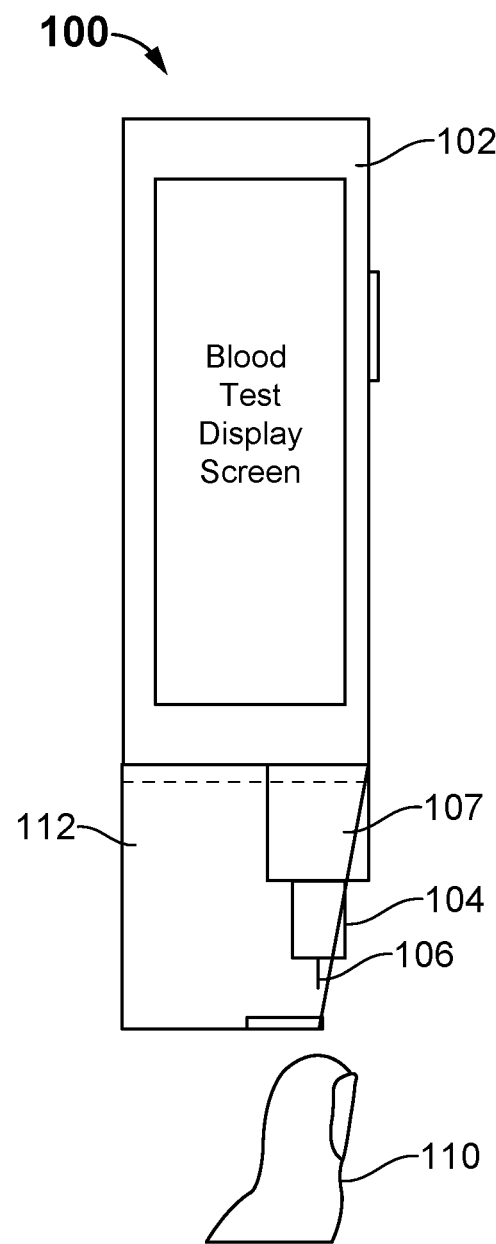
FIG. 5 shows a side view of the health monitoring system in one embodiment of the present invention.

Referring to FIG. 5, the finger pricking device 106 disposed in the center portion of the test strip assembly 104. In one embodiment, a cover 112 is disposed at a bottom portion of the test strip assembly 104. In one embodiment, the cover 112 is in a half-opened shaped structure to access the test strip assembly 104 and insert the finger pricking device 106. The cover 112 comprises an angular shape at a bottom portion and also opened on the side to insert the test strip assembly 104 with the finger pricking device 106 without opening the cover 112. In one embodiment, the cover 112 is made of a material, but not limited to, transparent material.

Figure 6:
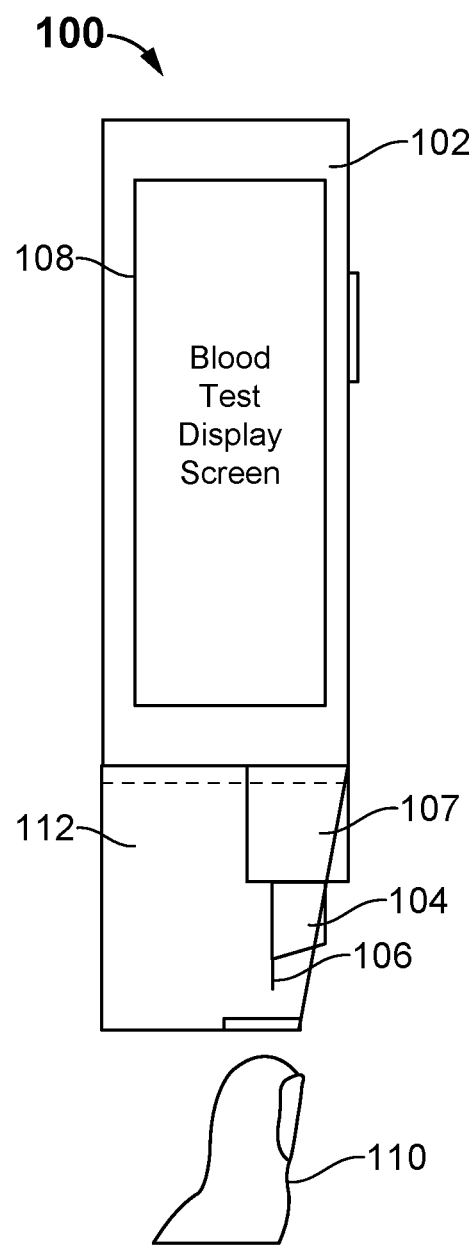
FIG. 6 shows a side view of the health monitoring system in another embodiment of the present invention.

Referring to FIG. 6, the finger pricking device 106 disposed at the extended edge of the tapered side of the test strip assembly 104. In one embodiment, test strip assembly 104 comprises the tapered side on any one of the side portions. In another embodiment, the test strip assembly 104 comprises a tapered side at the bottom portion. In one embodiment, the monitor 108 is configured to wirelessly transfer information related to the concentration of the blood sample and related test parameters of the user to another user communication device such as, but not limited to, a smartphone, a computer, a laptop, a PDA, and a tablet via a wireless network. In one embodiment, the user could place the blood drop on the test strip assembly 104 for detecting the concentration of the blood sample.

Figure 7:
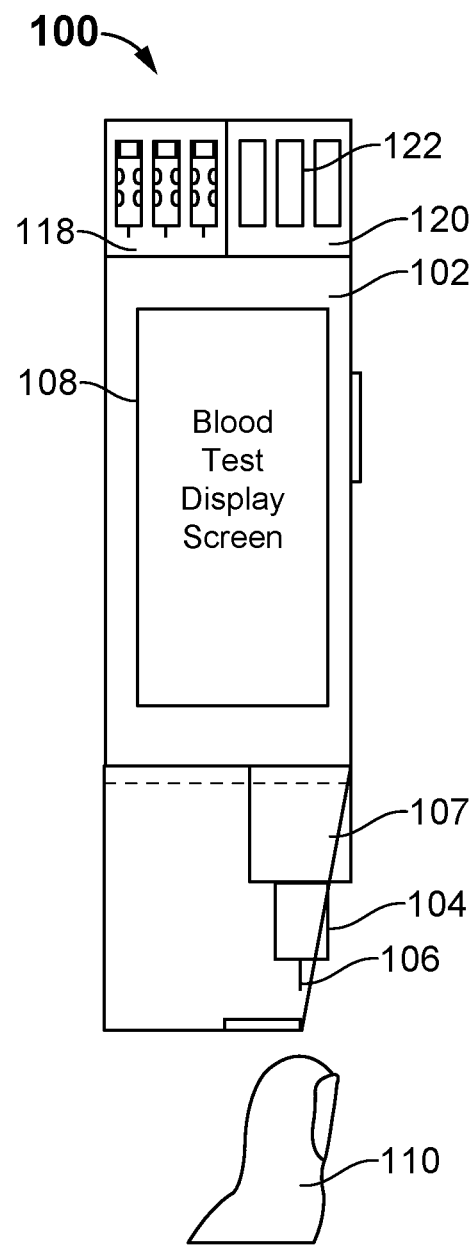
FIG. 7 shows a side view of the health monitoring system that includes one or more slots/chambers in one embodiment of the present invention.

Referring to FIG. 7, the housing 102 of the system 100 further comprises one or more slots/chambers (118 and 120). In one embodiment, the chambers (118 and 120) are positioned on, but not limited to, the top portion of housing 102. In one embodiment, the chamber 118 is configured to provide a place for storing a plurality of combination of a test strip assembly 104 and the finger pricking device 106. In one embodiment, the chamber 120 is configured to provide a place for storing a plurality of alcohol strips 122. The alcohol strips 122 could be used for cleaning the pricking area of a user's body, for example, but not limited to, the user's finger 110.

Figure 8:
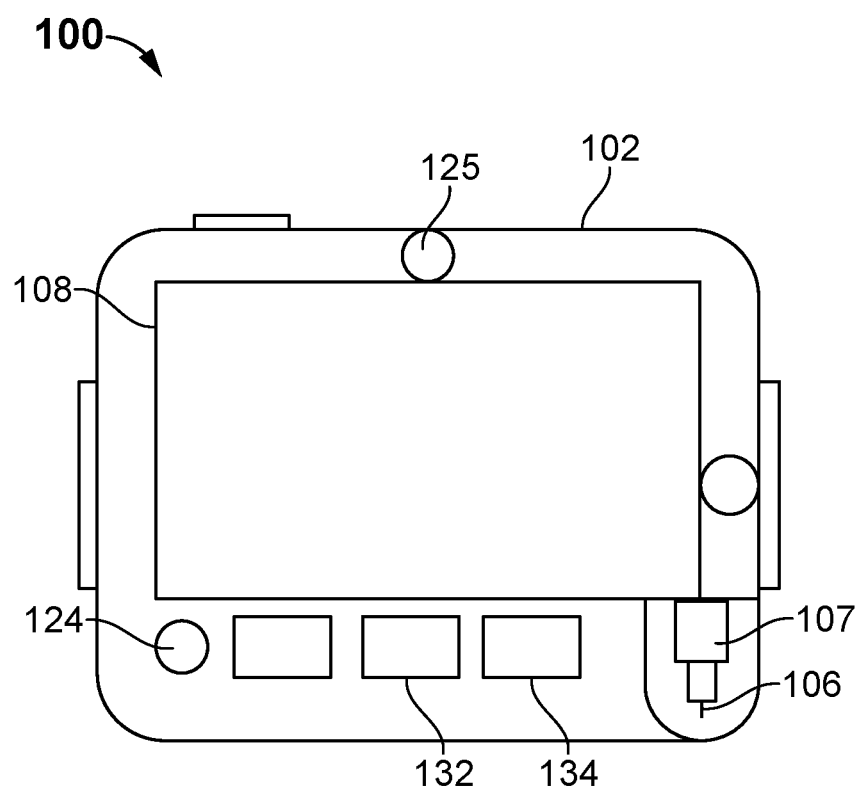
FIG. 8 shows a front view of the health monitoring system that includes a monitor in one embodiment of the present invention.

Referring to FIG. 8, the system 100 further comprises a light-based blood testing meter 124. In one embodiment, the light-based blood testing meter 124 could be used as a laser. In one embodiment, the light-based blood testing meter 124 is configured to test blood when the body part of the user is placed against the surface of the light-based blood testing meter 124. In one embodiment, the system 100 further comprises a scanner. The scanner could be positioned on a back side of the housing 102 of the system 100. In one embodiment, the scanner is configured to scan the body part of the user to check blood sugar levels. In one embodiment, the scanner could transfer the information related to blood sugar levels of the user via the wireless communication to the monitor 108 of the system 100 and the user communication device.

Figure 9:
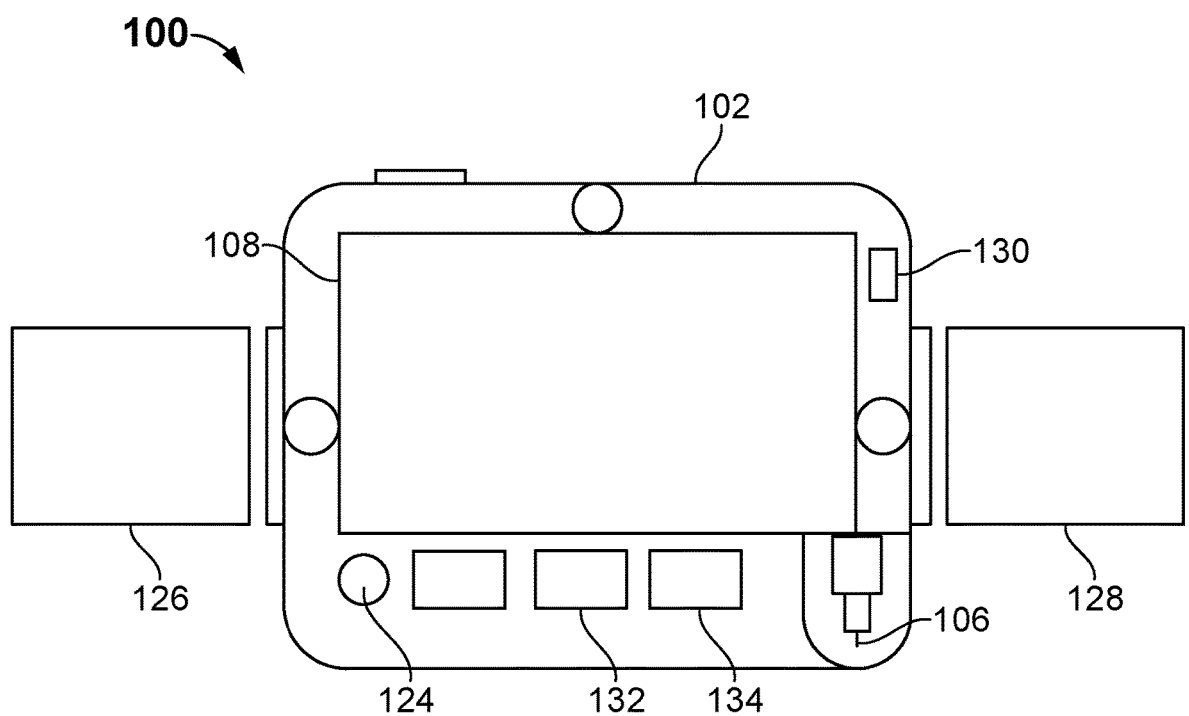
FIG. 9 shows a front view of the health monitoring system includes one or more blood pressure straps in one embodiment of the present invention.

Referring to FIG. 9, the system 100 further comprises one or more blood pressure straps (126 and 128). The blood pressure straps (126 and 128) could be removably mounted on the housing 102 of the system 100. In one embodiment, the blood pressure straps (126 and 128) are configured to measure the blood pressure of the user. The blood pressure straps (126 and 128) are also used for measuring the weight of the user by the placement of these straps under the feet of a person or an object. In one embodiment, the blood pressure straps (126 and 128) could be recharged via a wireless power transmission system or by its direct attachment to the main device. In one embodiment, the system 100 further includes a heart rate monitor (132 and 134). The user could place the fingers (i.e., left and right hand) on the heart rate monitor (132 and 134) for measuring the heart rate of the user. In one embodiment, the system 100 further comprises a height measuring detector light. The height measuring detector light is configured to measure the height of the user.

In one embodiment, the system 100 further comprises camera lenses. In one embodiment, the camera lenses are configured to capture images for diagnosing the user's body. In one embodiment, the camera lenses could be an X-ray scanner. In one embodiment, the system 100 further comprises an emergency alerting system 130. In one embodiment, the emergency alerting system 130 includes an audio and video call button with GPS auto-location. In one embodiment, the monitor 108 further comprises a plurality of input and output data ports. In one embodiment, the plurality of input and output ports are configured to transmit and receive the information related to health conditions such as, the concentration of the blood sample and related test parameters of the user via the user communication device. In one embodiment, the system 100 further includes a flashlight positioned on, but not limited to, the back side of the housing 102.

Figure 10:
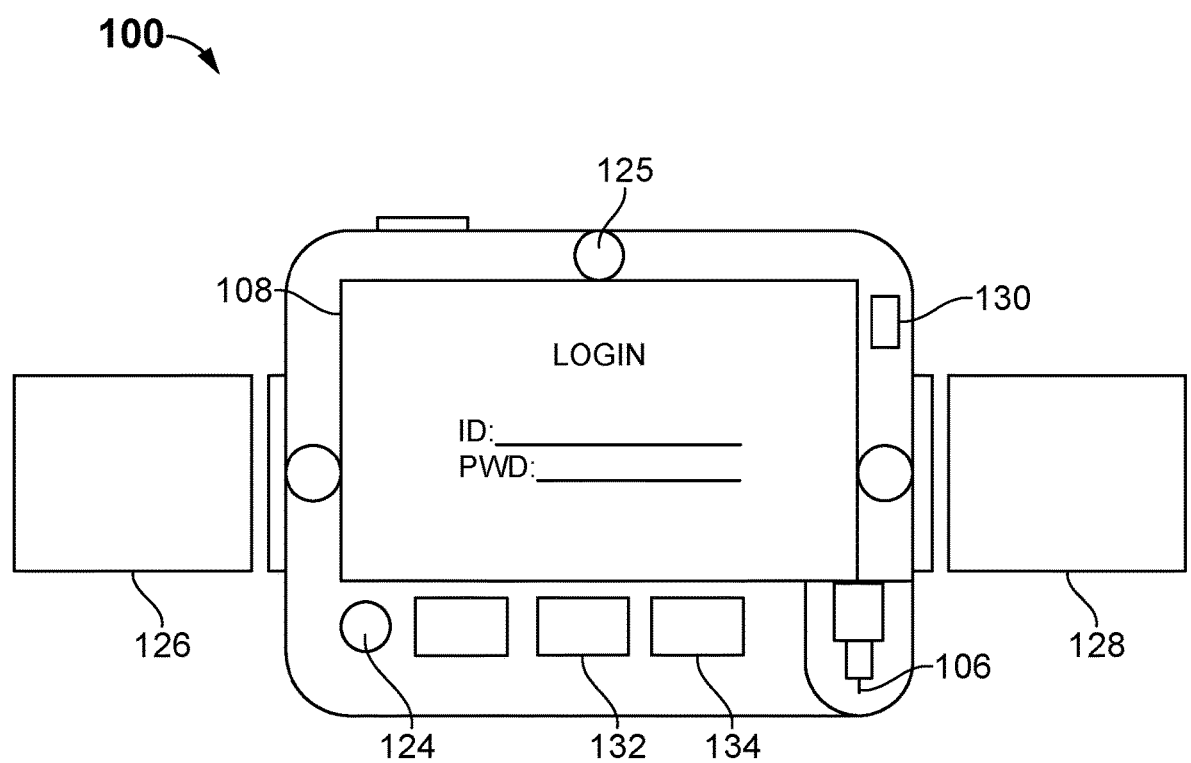
FIG. 10 shows a front view of the health monitoring system that includes a multi-factor authentication system in one embodiment of the present invention.

Referring to FIG. 10, the system 100 further comprises a multi-factor authentication system. In one embodiment, the multi-factor authentication system is configured to authenticate the user for logging into the user's profile. In one embodiment, the multi-factor authentication system includes, but not limited to, a fingerprint authentication 127, a facial feature authentication 125, and a password-based authentication. In an exemplary embodiment, the user could also login into the user's profile via the facial feature authentication 125. In another embodiment, the user could also login into the user's profile by placing the finger on the fingerprint authentication 127. In one embodiment, the fingerprint authentication 127 could be a contactless fingerprint scanner. In another embodiment, the fingerprint authentication 127 could be a contact fingerprint scanner. In some embodiments, the user could also login into the user's profile by entering credentials such as user ID and password via the password-based authentication.

Figure 11:
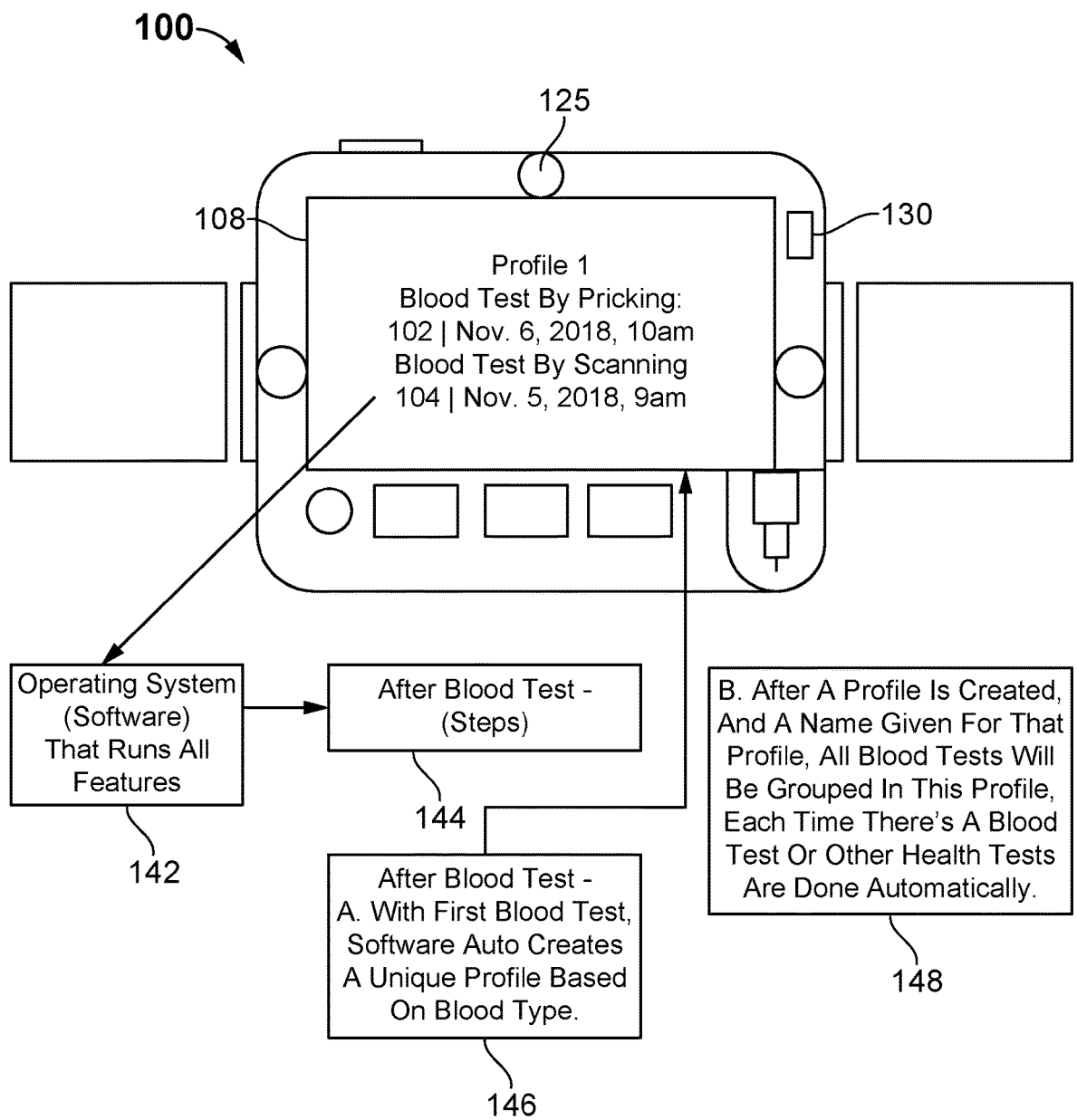
FIG. 11 shows a screenshot of the health monitoring system that automatically creates a profile for a user in one embodiment of the present invention.

Referring to FIG. 11, the system 100 configured to automatically creates a profile for the user. In one embodiment, the system 100 creates the profile for the user based on the blood type. After completion of the profile, the system 100 assigns a name for that profile and classifies the information related to the concentration of the blood samples, time, date, and blood test by pricking or scanning, and related test parameters in the profile. In one embodiment, the information related to the concentration of the blood samples and other test parameters will be automatically classified and stored in the generated profiles. Another unique feature is that the fingerprint authentication 127 could also detect the age, gender, and skin of the user and store that information with a picture of the user in the user's profile.

In one embodiment, a method for creating a profile for the user based on the patient's blood sample tests is disclosed. At step 142, the system 100 is operated for conducting test on the blood sample of the user. At step 144, the blood sample is tested using the combination of the test strip assembly 104 (shown in FIG. 1) and the finger pricking device 106 (shown in FIG. 1). At step 146, the system 100 automatically creates a unique profile based on blood type. Further, at step 148, the system 100 assigns a name for the generated profile and all blood tests will be classified and grouped in the generated profile. The system 100 stores all future tests if it is of the same blood type under the generated profile. In one embodiment, the user could change the name of the generated profile. All other tests that are done in the future like blood pressure, different methods used for blood testing, heart rate and such will be stored under the same profile based on the detection of each particular user via the multi-factor authentication system.

Figure 12:
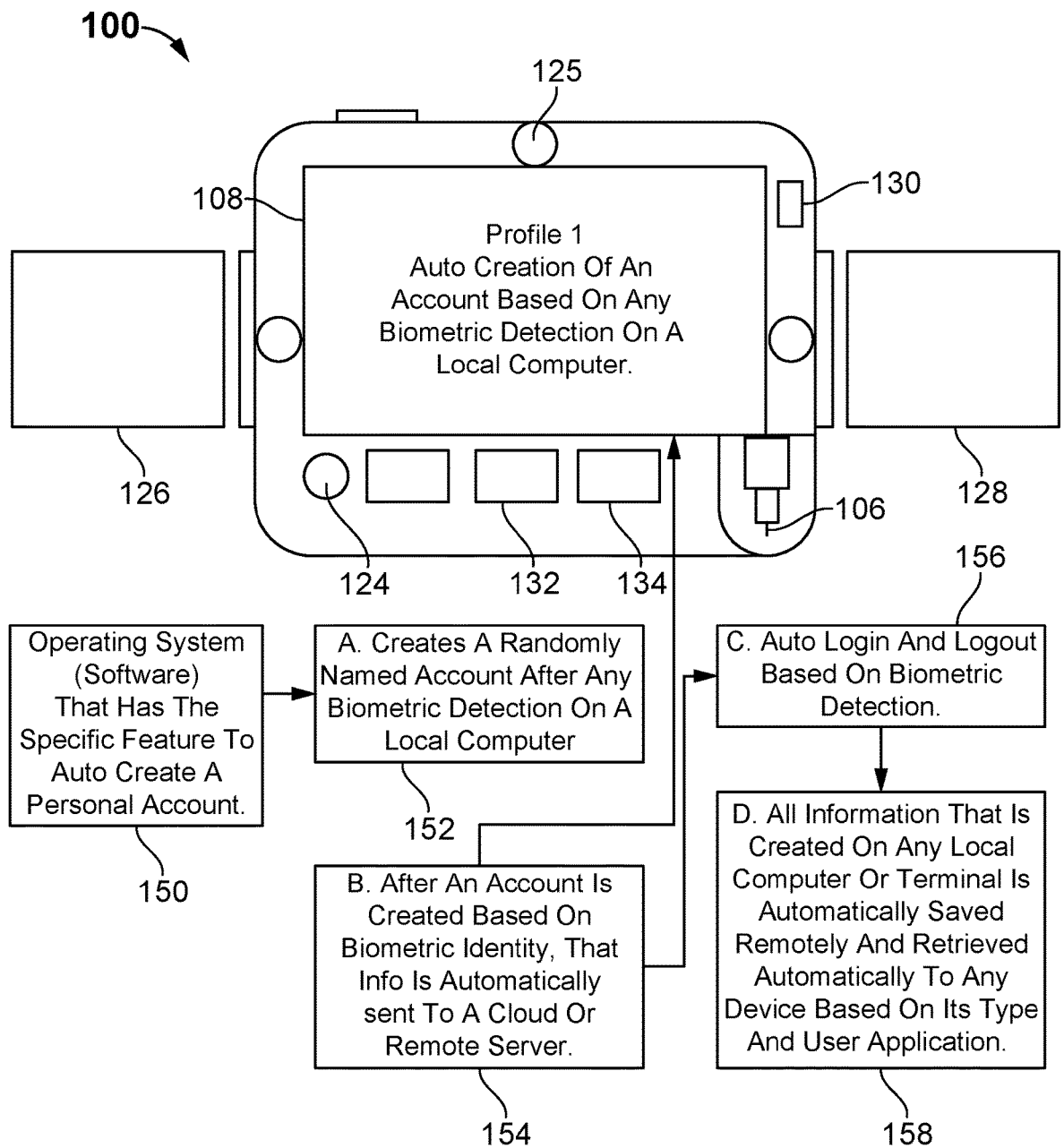
FIG. 12 shows a screenshot of the health monitoring system that automatically creates a profile for a user based on the multifactor authentication system in one embodiment of the present invention.

Referring to FIG. 12, the system 100 configured to create an account for the user based on the multi-factor authentication system. In one embodiment, the system 100 could automatically create accounts based on the multi-factor authentication system that includes, but not limited to, the facial feature authentication 125, the fingerprint authentication 127 and a password-based authentication. After completion of the account, the information related to the account is automatically sent to a cloud or remote server. In one embodiment, the user could automatically login and logout into the account via the multi-factor authentication such as, but not limited to, the facial feature authentication 125 or the fingerprint authentication 127. In one embodiment, the information related to the account could be automatically and remotely saved on any local computer, but not limited to, the user's communication device. In one embodiment, the information related to the account could be automatically retrieved to the user communication device such as, but not limited to, a smartphone, a laptop, a computer, and a tablet based on its type and user application by the use of the multi-factor authentication system onboard any device.

In one embodiment, a method for creating an account for the user based on the multi-factor authentication system is disclosed. At step 150, the system 100 could authenticate the user via, but not limited to, the fingerprint authentication 127. At step 152, the system 100 creates a randomly named account after biometric detection on a local computer. At step 154, the system 100 sends the information related to the account of the user to the server or cloud. At step 156, the user could automatically login or logout based on the biometric detection. Further, at step 158, the information related to the account of the user that is created on any local computer or terminal device is saved remotely and retrieved automatically to any device based on its type and user application.

Figure 13:
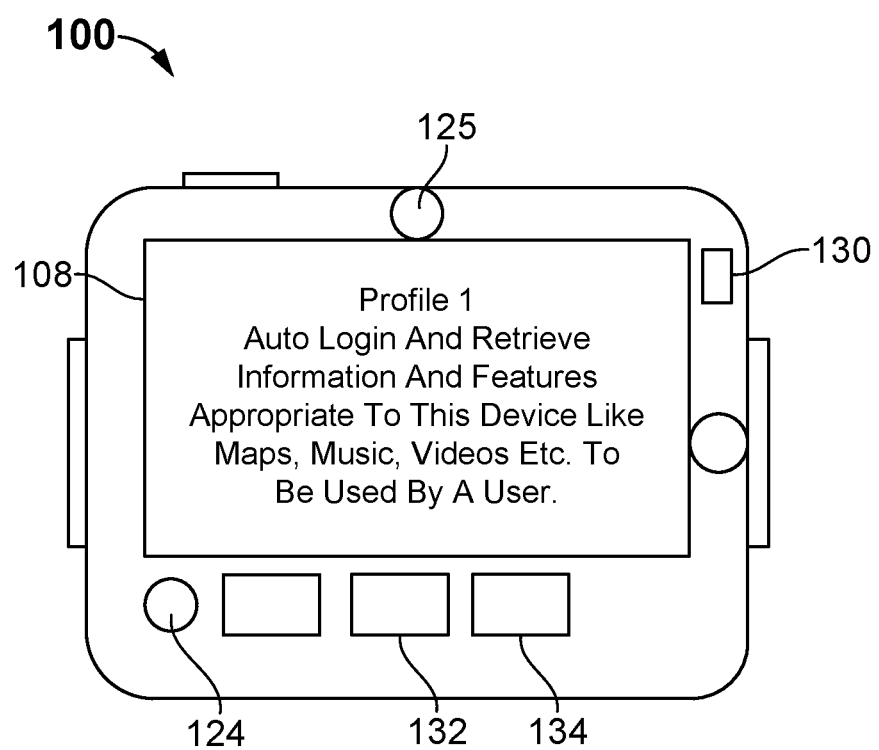
FIG. 13 shows a screenshot of the health monitoring system used for retrieving information on a vehicle in one embodiment of the present invention.

Referring to FIG. 13, the system 100 could provide automatically login for the user via the multi-factor authentication for retrieving information and features such as, but not limited to, car radio, maps, music, videos, etc. The multi-factor authentication includes such as, but not limited to, the facial feature authentication 125 or the fingerprint authentication 127, and the password-based authentication.

In one embodiment, the monitor 108 could be used in vehicles for different applications, for example, but not limited to, like a radio.

Figure 14:
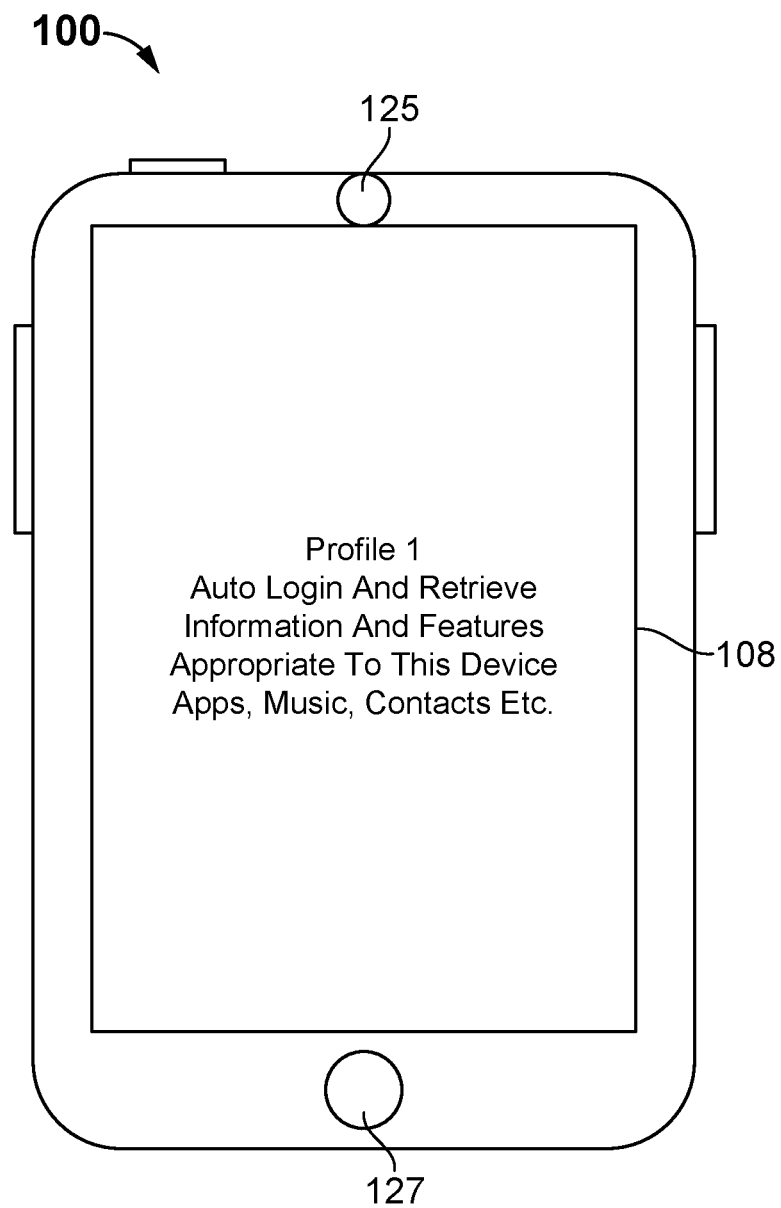
FIG. 14 shows a screenshot of the health monitoring system used in a smartphone in one embodiment of the present invention.

Referring to FIG. 14, the system 100 could provide automatically login for the user for retrieving information and features such as, but not limited to, applications, music, contacts, etc. via the monitor 108. The user could login via the multi-factor authentication such as, but not limited to, the facial feature authentication 125 or the fingerprint authentication 127, and the password-based authentication. In one embodiment, the monitor 108 could be used as a smartphone.

Figure 15:
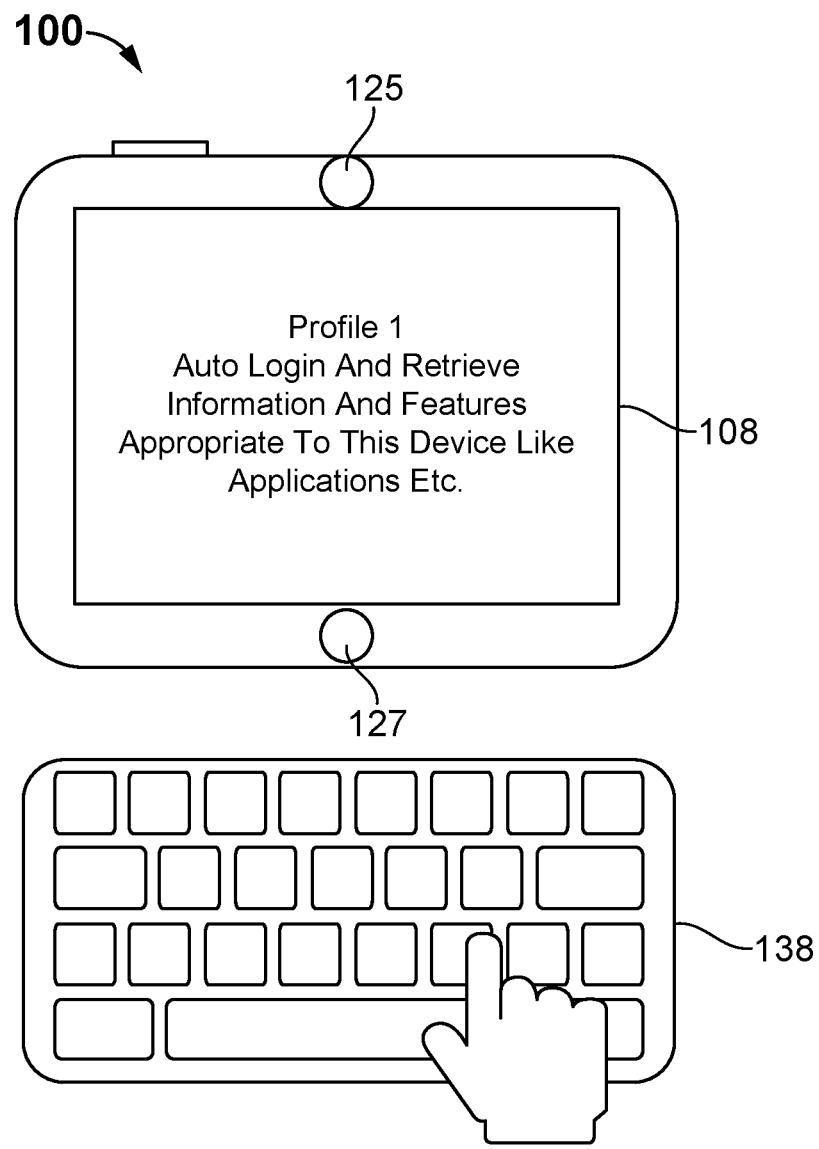
FIG. 15 shows a screenshot of the health monitoring system used in a computer in one embodiment of the present invention.

Referring to FIG. 15, the system 100 could provide automatically login for the user for retrieving the information and features, for example, but not limited to, applications via the monitor 108 and a user interface 138. The user could login via the multi-factor authentication such as, but not limited to, the facial feature authentication 125 or the fingerprint authentication 127, and the password-based authentication. In one embodiment, the monitor 108 could be used as a computer or a laptop.

Figure 16:
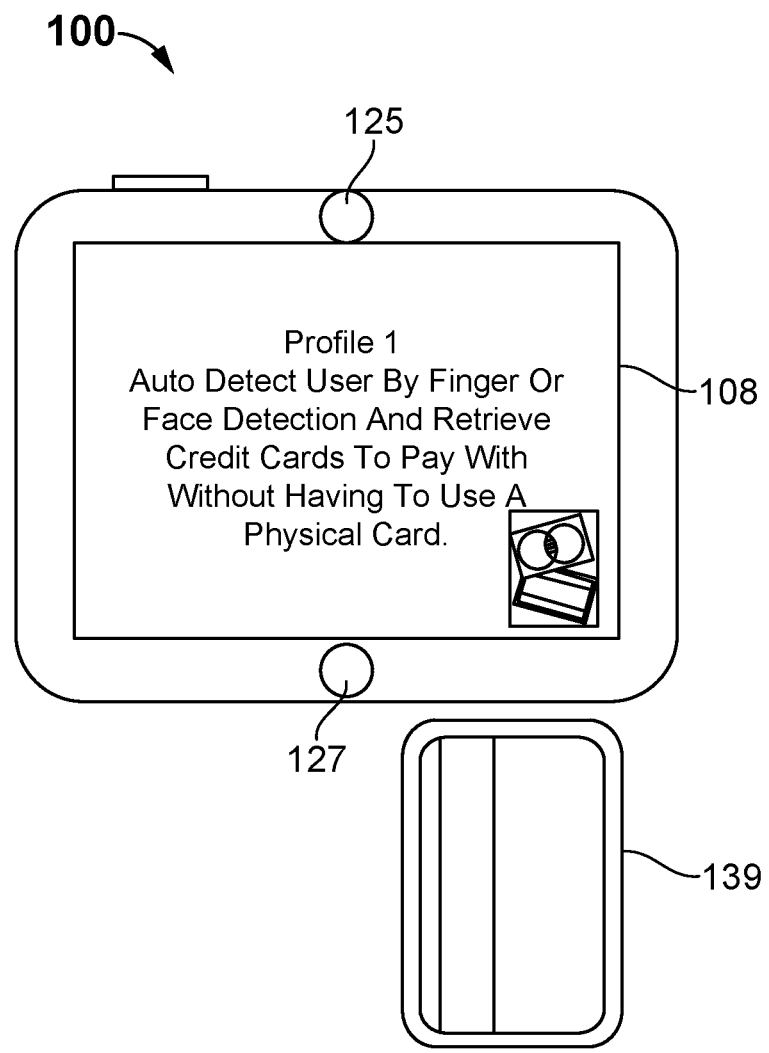
FIG. 16 shows a screenshot of the health monitoring system used in a credit card terminal in one embodiment of the present invention.

Referring to FIG. 16, the system 100 could automatically detect the user via the multi-factor authentication such as, but not limited to, the facial feature authentication 125 or the fingerprint authentication 127, and the password-based authentication for retrieving the information related to credit cards 139 to pay via the monitor 108 without having the credit card physically. In one embodiment, the monitor 108 could be used as a credit card terminal or a point-of-sale (POS).

Figure 17:
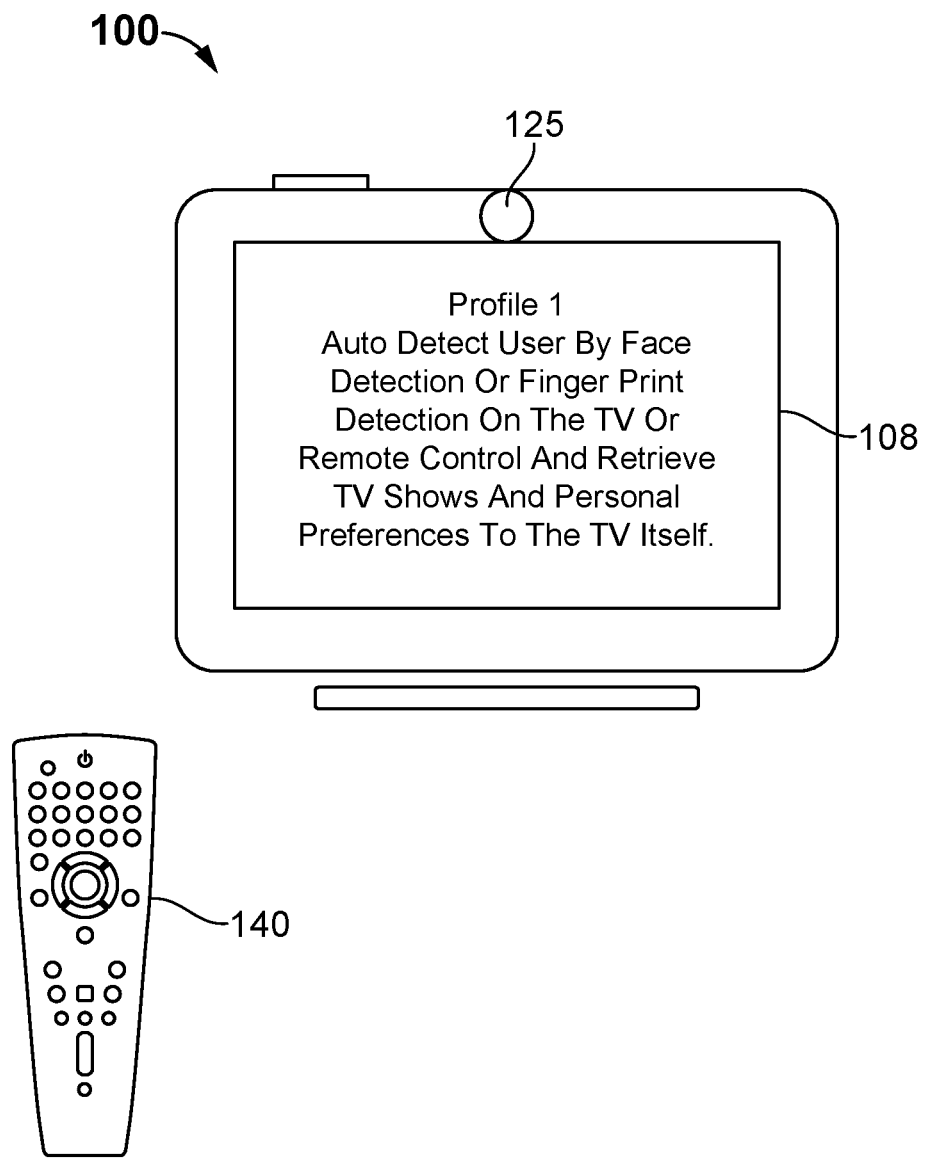
FIG. 17 shows a screenshot of the health monitoring system used in an entertainment device/TV in one embodiment of the present invention.

Referring to FIG. 17, the system 100 could automatically and remotely detect the user on the entertainment device/TV or remote control 140 via the multi-factor authentication such as, but not limited to, the facial feature authentication 125 or the fingerprint authentication 127 for retrieving previously created and stored personalized entertainment shows via the monitor 108. In one embodiment, the monitor 108 could be used as the entertainment device/TV.

Figure 18:
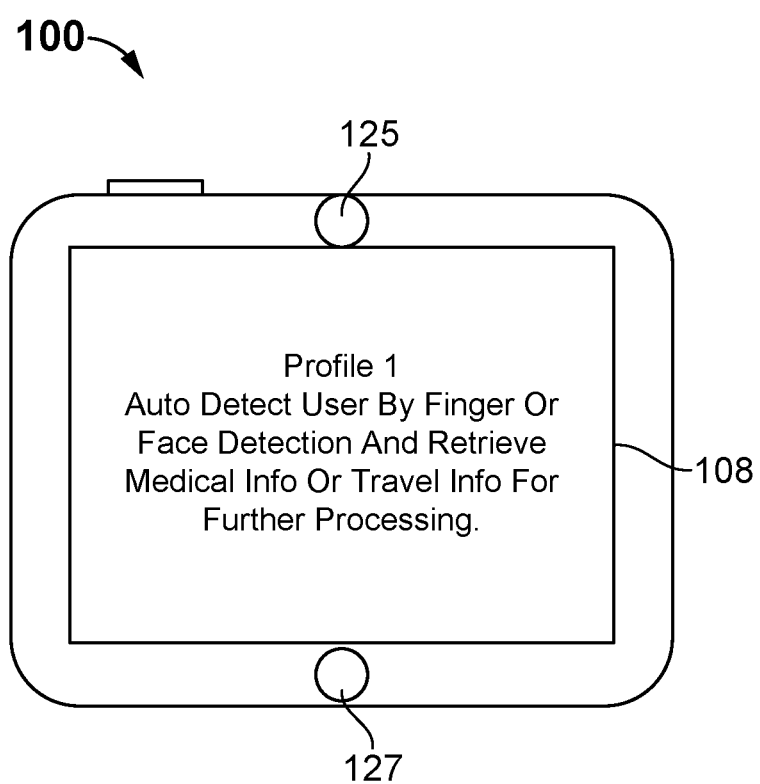
FIG. 18 shows a screenshot of the health monitoring system used as a medical or travel terminal in one embodiment of the present invention.

Referring to FIG. 18, the system 100 could automatically detect the user via the multi-factor authentication such as, but not limited to, the facial feature authentication 125 or the fingerprint authentication 127 and the password-based authentication for retrieving the information via the monitor 108 related to, but not limited to, medical and travel information. In one embodiment, the monitor 108 could be used as a medical or travel terminal.

In one embodiment, the monitor 108 has an emergency two-way calling feature. In one embodiment, the monitor 108 further comprises a USB slot for inserting a storage device, such as but not limited to, a memory card for storing and transmitting information to other user communication devices such as, but not limited to, a smartphone, a computer, a laptop, and a tablet via a wired or wireless communication system.

Referring FIG. 19-FIG. 25, in another embodiment, the system comprises a remote data storage server 902, an automated operating system 904, a multi-factor biometric authentication system 906 and a user device. In one embodiment, the remote data storage server 902, the automated operating system (AOS) 904, the multi-factor biometric authentication system 906 and the user device or interface configured to communication and share data via auto sync configuration. The automated operating system 904 communicates with the user device via a module 915 to send and receive device information from AOS 904 and auto install and restore system to operate. The authentication system 906 utilizes at least any of one of the authentication methods, including, but not limited to password login 908, blood test based 910, facial recognition 912 or a finger print 914. The multi-factor authentication system 906 is configured to authenticate a user for logging into the user's profile. The information related to the user is presented in a readable form to the user via an output device 916.

Figure 19:
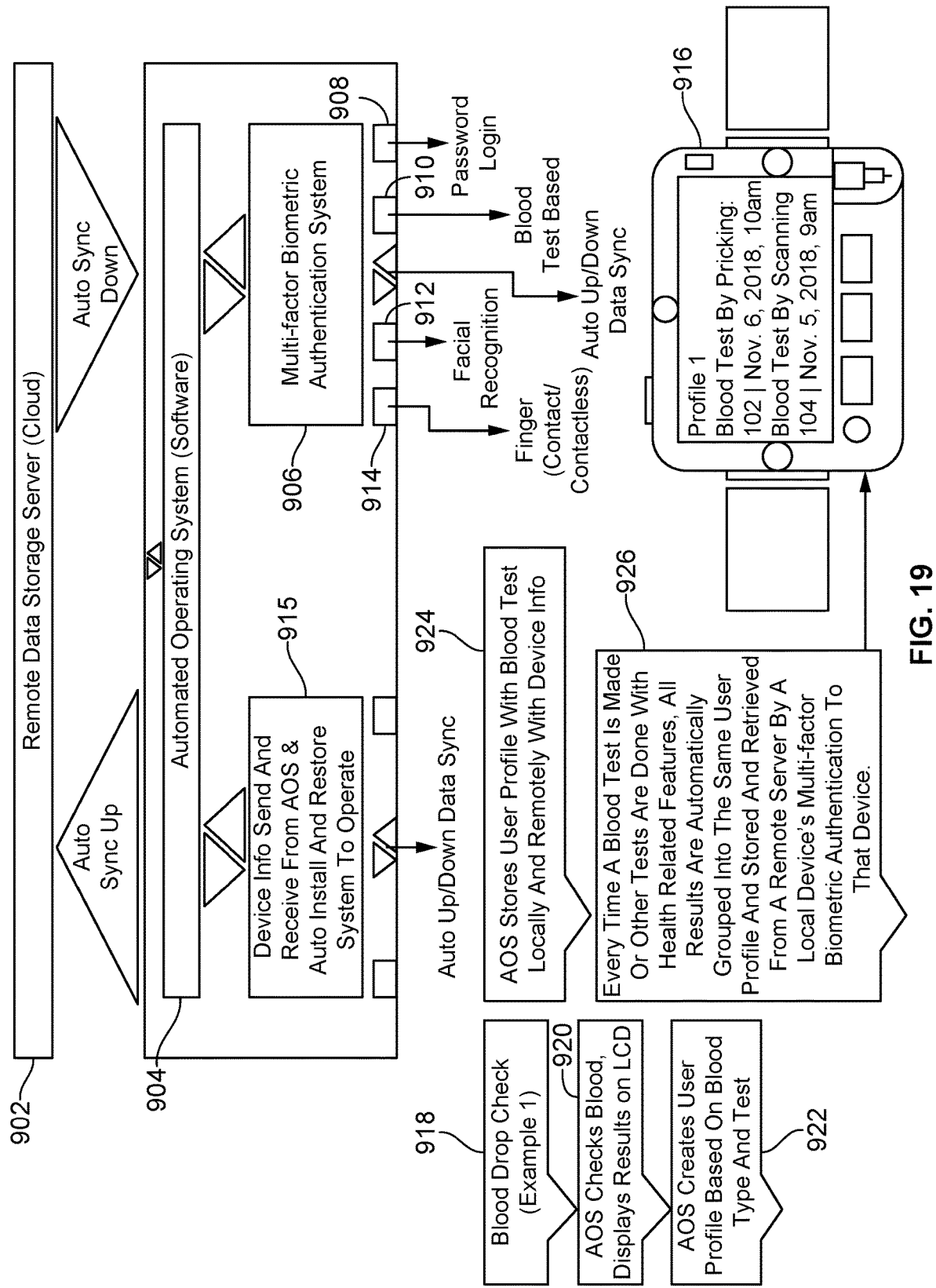
FIG. 19 illustrates a block diagram of a health monitoring system according to an embodiment of the present invention.

Referring to FIG. 19, at block 918, blood drop check initiates. At block 920, the AOS 904 checks and displays results on the output device 916 such as LCD. At block 922, the AOS 904 creates a user profile based on blood type and test. At block 924, The AOS 904 stores a user profile with blood test locally and remotely with device info. At block 926, every time a blood test is made or other tests are done with health-related features, all results are automatically grouped into the same user profile and stored and retrieved from a remote server 902 by a local device's multi-factor biometric authentication to that device.

Figure 20:
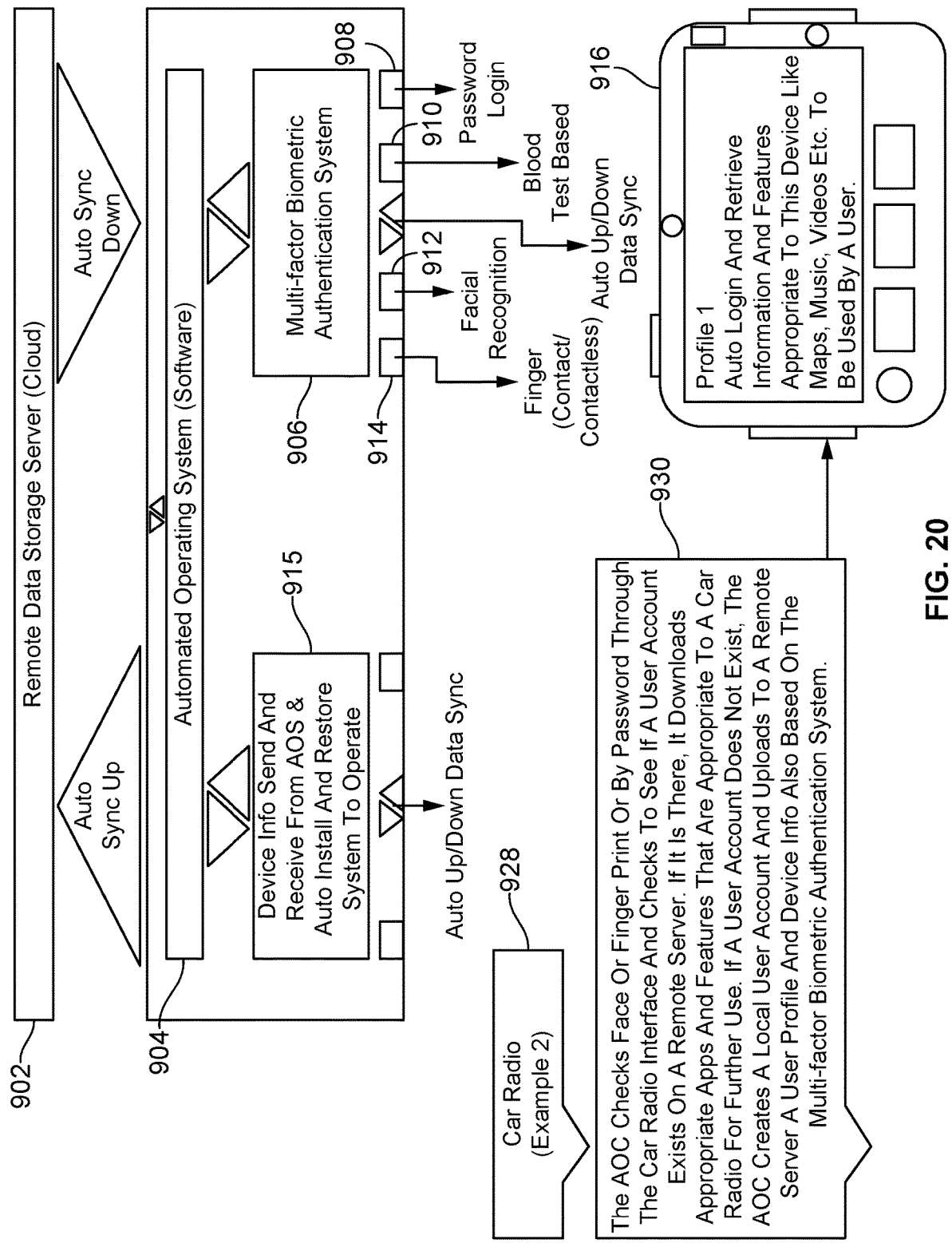
FIG. 20 illustrates a block diagram of a health monitoring system comprising a car radio interface according to an embodiment of the present invention.

Referring to FIG. 20, the multi-factor biometric authentication system 906 utilizing user interface such as car radio 928 for performing authentication function is disclosed. At block 930, the AOS 904 checks face or finger print or by password through the car radio 928 interface and checks to see if a user account exists on the remote server 902. If it is there, it downloads appropriate apps and features that are appropriate to a car radio 928 for further use. If a user account does not exist, the AOS 904 creates a local user account and uploads to a remote server 902 a user profile and device info also based on the multi-factor biometric authentication system.

Figure 21:
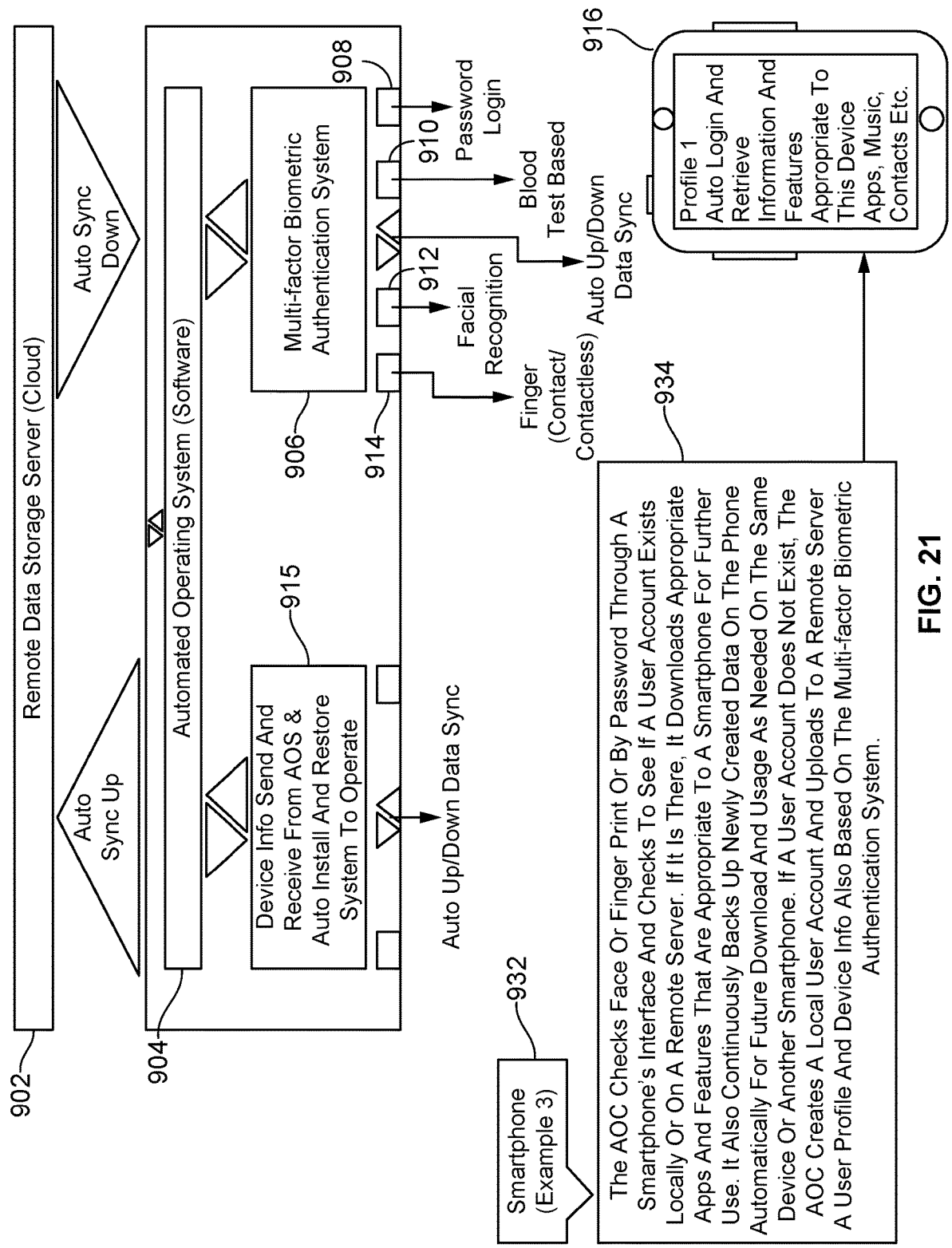
FIG. 21 illustrates a block diagram of a health monitoring system comprising a smartphone interface according to an embodiment of the present invention.

Referring to FIG. 21, the user interface is a smartphone 932. At block 934, the AOC 904 checks face or finger print or by password through a smartphone's 932 interface and checks to see if a user account exists locally or on a remote server 902. If it is there, it downloads appropriate apps and features that are appropriate to the smartphone 932 for further use. It also continuously backs up newly created data on the phone 932 automatically for future download and usage as needed on the same device or another smartphone. If a user account does not exist, the AOS 904 creates a local user account and uploads to the remote server 902 a user profile and device info also based on the multi-factor biometric authentication system 906.

Figure 22:
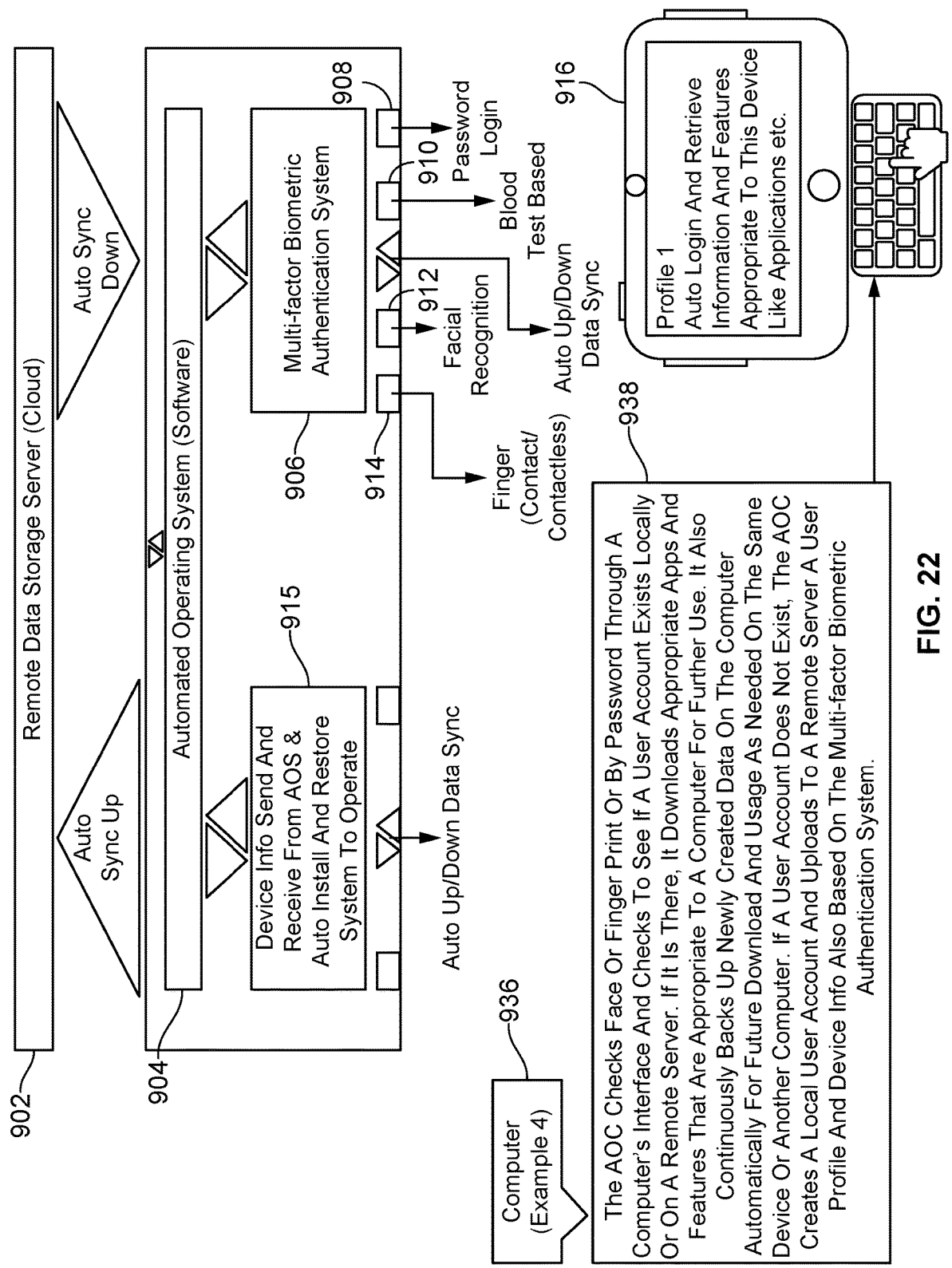
FIG. 22 illustrates a block diagram of a health monitoring system comprising a computer interface according to an embodiment of the present invention.

Referring to FIG. 22, the user interface is a computer 934. At block 938, the AOS 904 checks face or finger print or by password through a computer's interface 936 interface and checks to see if a user account exists locally or on a remote server 902. If it is there, it downloads appropriate apps and features that are appropriate to the computer's interface 936 for further use. It also continuously backs up newly created data on the computer 936 automatically for future download and usage as needed on the same device or another computer. If a user account does not exist, the AOS 904 creates a local user account and uploads to the remote server 902 a user profile and device info also based on the multi-factor biometric authentication system 906.

Figure 23:
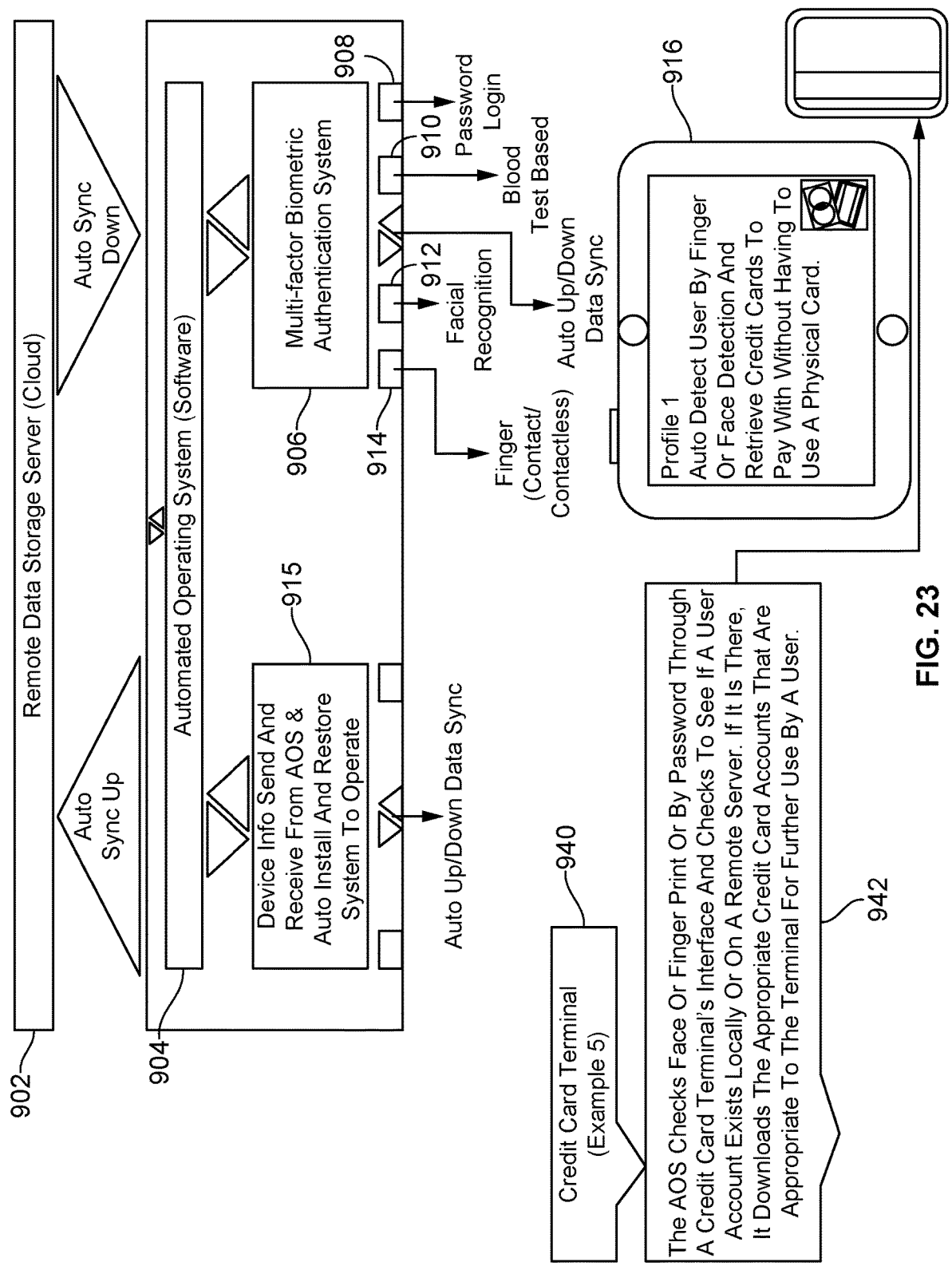
FIG. 23 illustrates a block diagram of a health monitoring system comprising a credit card terminal interface according to an embodiment of the present invention.

Referring to FIG. 23, the user interface is a credit card terminal 940. At block 942, the AOS 904 checks face or finger print or by password through a credit card terminal's 940 interface and checks to see if a user account exists locally or on a remote server 902. If it is there, it downloads the appropriate credit card accounts that are appropriate to the terminal for further use by a user.

Figure 24:
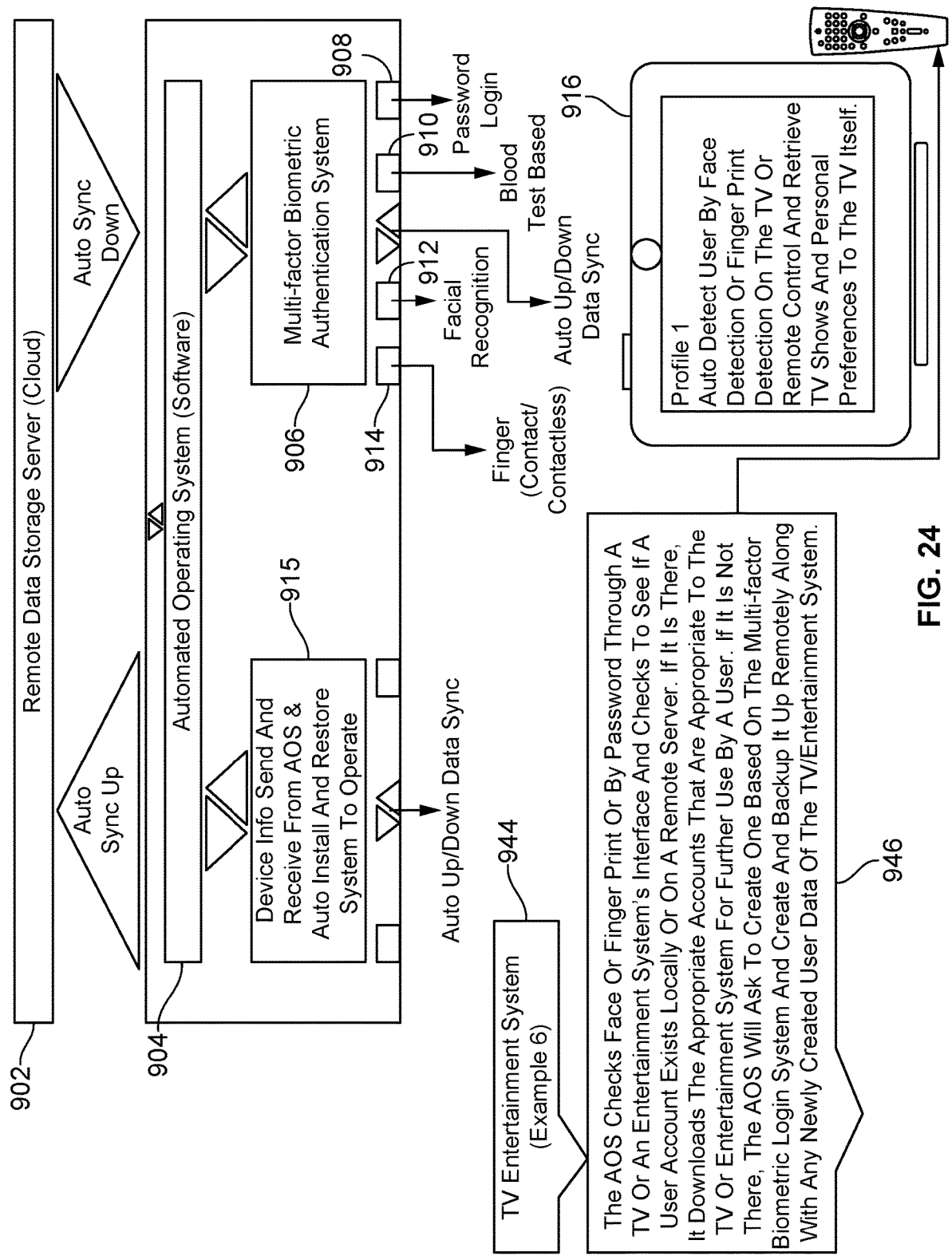
FIG. 24 illustrates a block diagram of a health monitoring system comprising a TV entertainment system interface according to an embodiment of the present invention.

Referring to FIG. 24, the user interface is a TV or an entertainment system 944. At block 946, the AOC 904 checks face or finger print or by password through a TV entertainment system 944 interface and checks to see if a user account exists locally or on a remote server 902. If it is there, it downloads appropriate apps and features that are appropriate to the TV entertainment system 944 for further use. If is not there, the AOS 904 will ask to create one based on the multi-factor biometric login system and create and backup it up remotely along with any newly created user data of the tv/entertainment system 944.

Figure 25:
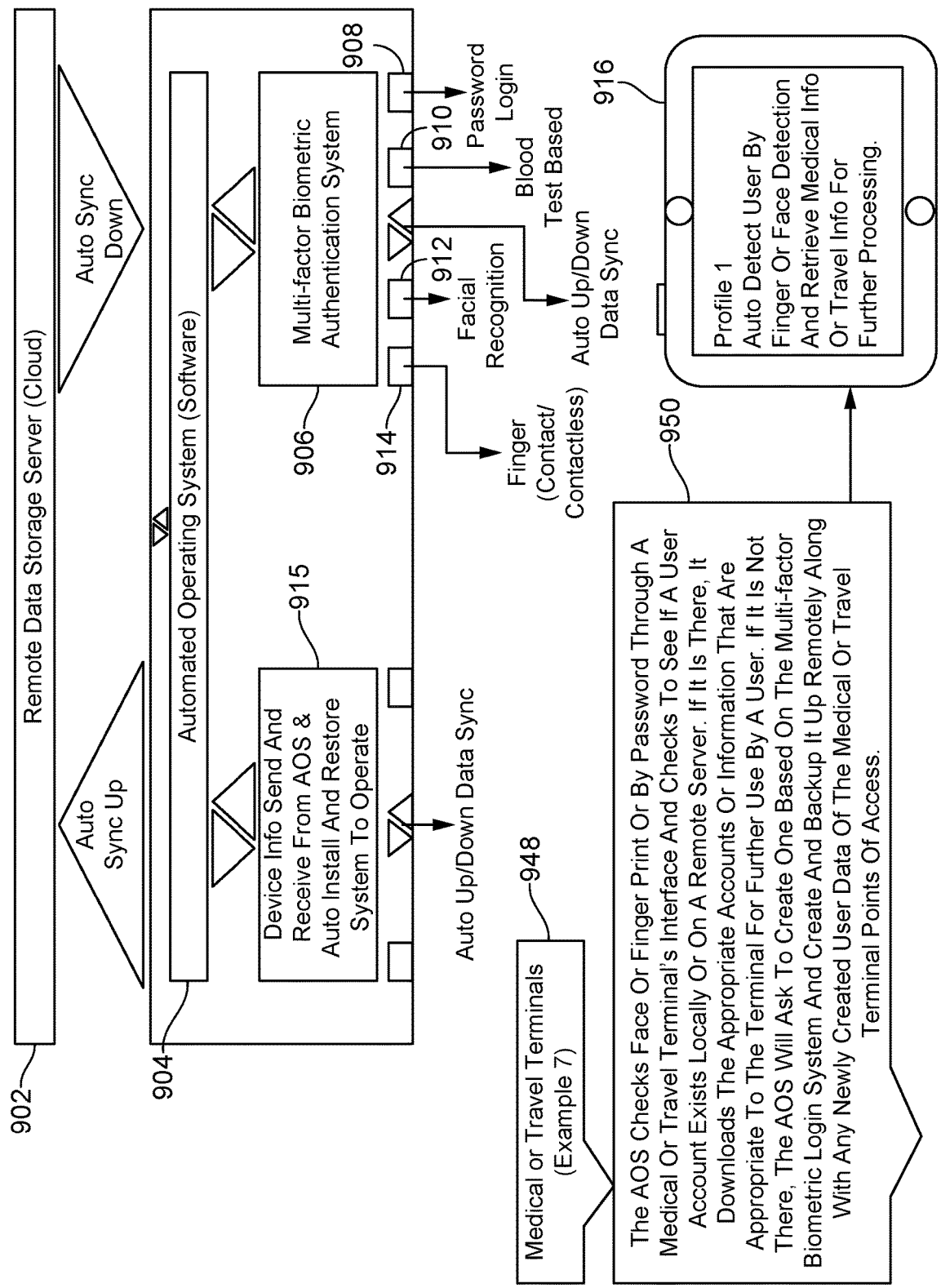
FIG. 25 illustrates a block diagram of a health monitoring system comprising a medical or travel terminal interface according to an embodiment of the present invention.

Referring to FIG. 25, the user interface is a medical or travel terminal 948. At block 950, the AOS 904 checks face or finger print or by password through a medical or travel terminal's 948 interface and checks to see if a user account exists locally or on a remote server 902. If it is there, it downloads the appropriate accounts or information that are appropriate to the terminal 948 for further use by a user. If it is not there, the AOS 904 will ask to create one based on the multi-factor biometric login system and create and backup it up remotely along with any newly created user data of the medical or travel terminal 948 points of access.

Although a single embodiment of the invention has been illustrated in the accompanying drawings and described in the above detailed description, it will be understood that the invention is not limited to the embodiment developed herein, but is capable of numerous rearrangements, modifications, substitutions of parts and elements without departing from the spirit and scope of the invention.

The foregoing description comprises illustrative embodiments of the present invention. Having thus described exemplary embodiments of the present invention, it should be noted by those skilled in the art that these within the disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A health monitoring system, comprising:
a housing, wherein the housing includes a top portion and a bottom portion;
a test strip assembly disposed in the bottom portion of the housing, wherein the test strip assembly comprises a tapered side on one side of the bottom portion;
a finger pricking device disposed on an extended edge of the tapered side of the test strip assembly, wherein the finger pricking device is integrated to a plunger to prick a body part of a user via a plunger mechanism for availing a blood sample;
a transparent cover disposed at a bottom portion of the test strip assembly, wherein the transparent cover is in a half-opened shaped structure to access the test strip assembly and insert the finger pricking device, comprises an angular shape at a bottom portion and opened on one side to insert the test strip assembly without opening the transparent cover;
a monitor disposed in the housing, wherein the monitor is configured to display the concentration of the blood sample, the monitor comprising a processor and a memory unit; and
a database in communication with the monitor for storing information related to the concentration of the blood sample and related test parameters of a user;
wherein the memory unit stores a set of program modules, and wherein the processor in communication with the memory unit, configured to execute the set of program modules, wherein the set of program modules comprises,
a profile creation module configured to automatically create a profile of the user via a multi-factor authentication system, wherein the multi-factor authentication system configured to authenticate the user for automatic logging into the user's profile;
a description generation module configured to convert the information related to the concentration of the blood sample and related test parameters into a readable description, and
an output module configured to present a readable description to the user.

2. The system of claim 1, wherein the monitor is wirelessly communicated to a user communication device via a network, wherein the network includes at least one of Wi-Fi, Bluetooth®, WLAN, infrared, and radio waves.

3. The system of claim 2, wherein the user communication device is at least one of a tablet, a smartphone, PDA, a smartwatch, a computer, and a laptop.

4. The system of claim 1, further comprises blood pressure straps, wherein the blood pressure straps are also configured to measure the weight of a user by the placement of these straps under the feet of a person or an object.

5. The system of claim 1, wherein the blood pressure straps are rechargeable via a wireless power transmission system or by direct attachment to the main device or the present invention.

6. The system of claim 1, further comprises a height measuring detector light configured to measure the height of a user.

7. The system of claim 1, wherein the monitor further comprises a plurality of input and output data ports, wherein the plurality of input and output ports are configured to transmit and receive any data or information or data related to the concentration of the blood sample and related test parameters of the user to the user's communication devices.

8. The system of claim 1, wherein the monitor is at least one of a computer, a smartphone, a PDA, a tablet, a credit card terminal, a point of sale terminal (POS), an entertainment device or TV, a medical terminal, and a travel terminal.

9. The system of claim 1, wherein the housing further includes a plurality of slots, wherein the plurality of slots is configured to store a test strip assembly, finger pricking devices, and alcohol strips for cleaning a part of the user's body.

10. The system of claim 1, further comprises a heart rate monitor, wherein the heart rate monitor is configured to monitor and track the heart rate of the user.

11. The system of claim 1, further comprises an emergency alerting system, wherein the emergency alerting system includes an audio and video call button with GPS auto-location.

12. The system of claim 1, further comprises a removable camera lens, wherein the removable camera lens is configured to create X-ray images for diagnosing the user's body.

13. The system of claim 1, wherein the multi-factor authentication system includes a fingerprint authentication, a contactless fingerprint authentication, a facial feature authentication, and a password-based authentication.

* * * * *